United States Patent [19]

Sze

[11] 4,061,471
[45] Dec. 6, 1977

[54] MOLTEN SALT LIFT GAS SYSTEM FOR PRODUCTION OF CHLORINATED HYDROCARBONS

[75] Inventor: Morgan C. Sze, Upper Montclair, N.J.

[73] Assignee: The Lummus Company, Bloomfield, N.J.

[21] Appl. No.: 633,491

[22] Filed: Nov. 19, 1975

[51] Int. Cl.² .............. B01J 8/12; B01J 8/18; B01J 8/26; C07C 21/02
[52] U.S. Cl. ............................... 23/260; 23/283; 260/656 R
[58] Field of Search ............. 23/260, 283, 284, 288 G; 260/656 R

[56] References Cited
U.S. PATENT DOCUMENTS

| | | | |
|---|---|---|---|
| 2,463,623 | 3/1949 | Huff | 23/288 G |
| 3,149,924 | 9/1964 | Cross, Jr. | 23/288 G UX |
| 3,215,505 | 11/1965 | Schmanfeld et al. | 23/288 G X |
| 3,250,696 | 5/1966 | Schutte | 23/284 X |
| 3,838,039 | 9/1974 | Vesely et al. | 23/288 G X |
| 3,839,197 | 10/1974 | Greenwood et al. | 23/288 G X |
| 3,869,518 | 3/1975 | Sze et al. | 260/656 R X |

Primary Examiner—Morris O. Wolk
Assistant Examiner—Michael S. Marcus
Attorney, Agent, or Firm—Marn & Jangarathis

[57] ABSTRACT

In the production of chlorinated hydrocarbons by the use of molten salts wherein molten salt is oxidized in a first reactor and lifted by lift gas in a first lift gas circuit into a chlorinated hydrocarbon production reactor, with the molten salt withdrawn from the chlorinated hydrocarbon production reactor being lifted by a lift gas in a second lift gas circuit into the oxidation reactor, a single pressurized melt storage tank is connected to the first and second lift gas circuits to provide both control of flow rates and surge capacity.

2 Claims, 1 Drawing Figure

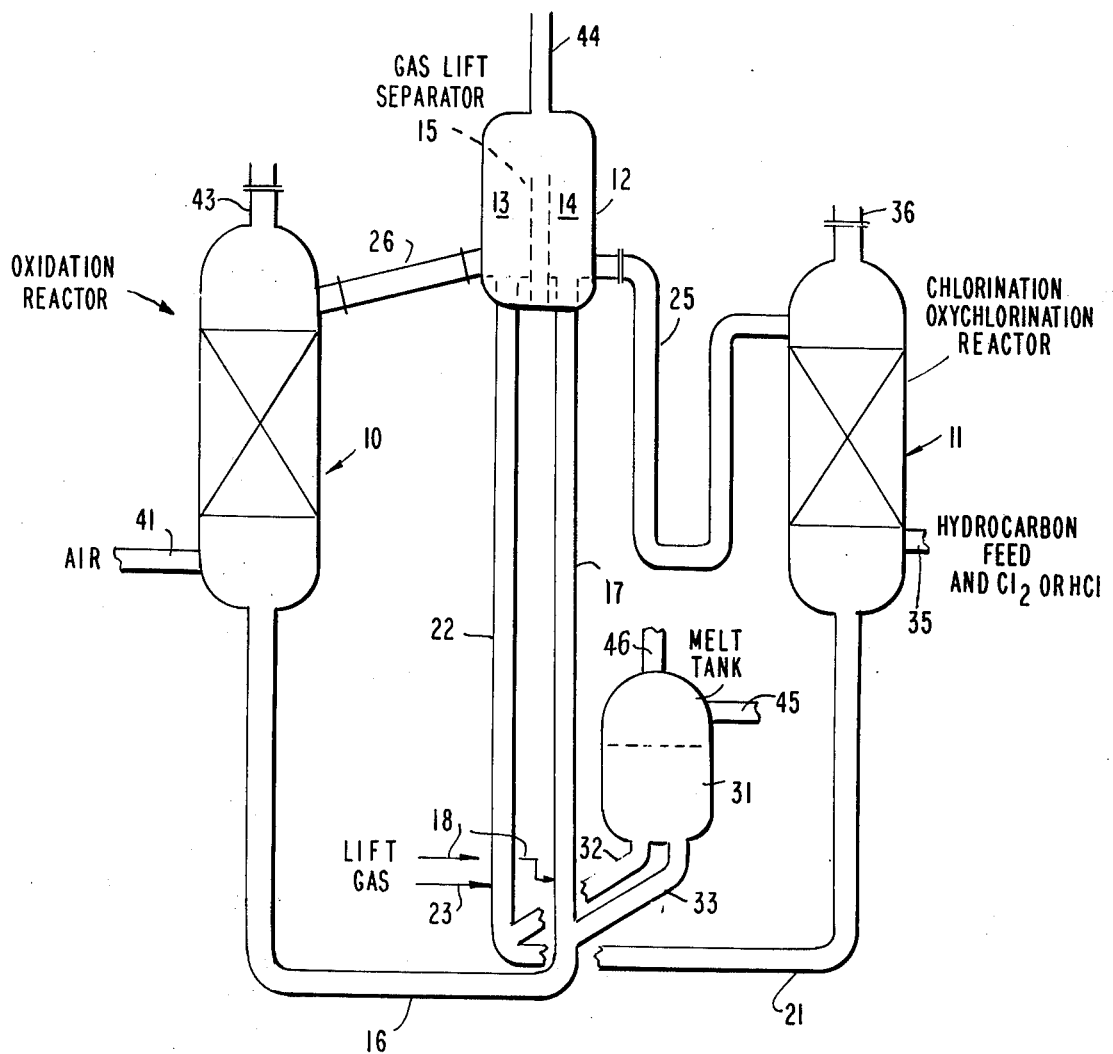

MOLTEN SALT LIFT GAS SYSTEM FOR PRODUCTION OF CHLORINATED HYDROCARBONS

This invention relates to the production of chlorinated hydrocarbons by the use of molten salts, and more particularly, to a new and improved lift gas system for introducing the molten salt into the reactors of a chlorinated hydrocarbon production system.

In producing chlorinated hydrocarbons by molten salts, in general, the process involves the use of two reactors, and two lift gas separators, with molten salt withdrawn from one reactor being lifted by a lift gas into one of the lift gas separators for introduction into the other reactor, and vice versa.

There is a need for an improvement in such systems in order to provide for control of salt flow rates and surge capacity at low capital costs.

Accordingly, an object of this invention is to provide for improved production of chlorinated hydrocarbons by the use of molten salts.

Another object of the present invention is to provide an improved lift gas system and process for introducing molten salts into reactors for producing chlorinated hydrocarbons by the use of molten salts.

In accordance with the present invention, there is provided a system and process for producing chlorinated hydrocarbons by the use of a molten salt which includes an oxidation reactor, a chlorinated hydrocarbon production reactor, a first lift gas circuit for transferring molten salt from the oxidation reactor to the chlorinated hydrocarbon production reactor, including a first lift gas pipe and a first separator for separating lift gas from the molten salt, a second lift gas circuit, including a second lift gas pipe and a second separator for separating lift gas from the molten salt, for transferring molten salt from the chlorinated hydrocarbon production reactor to the oxidation reactor, and a single pressurized molten salt storage tank connected to the first and second gas lift pipes for pressurizing the first and second lift gas pipes to control salt flow and to provide the required surge capacity.

The molten salt mixture employed for the production of a chlorinated hydrocarbon contains a chloride of a multivalent metal; i.e., a metal having more than one positive valence state, in its higher and lower valence state, such as the higher and lower valent chlorides of manganese, iron, copper, cobalt and chromium, preferably copper. The molten salt mixture also generally includes a metal salt melting point depressant which is non-volatile and resistant to the action of oxygen at the process conditions, such as an alkali metal chloride; in particular, potassium and lithium chloride, or a heavy metal chloride; i.e., heavier than copper, of Groups I, II, III and IV of the Periodic Table. A preferred molten salt mixture contains copper chlorides and potassium chlorides, with the potassium chloride generally being present in an amount from about 20% to about 40%, by weight.

The oxidation of the molten salt in the oxidation reactor is generally effected at a temperature of from about 600° F to about 1000° F, and preferably at a temperature from about 700° F to about 950° F. The pressure in the oxidation reactor is generally in the order of from about 1 to about 50 atmospheres.

The chlorinated hydrocarbon production reactor is generally operated at a temperature from about 600° F to about 1000° F, with the exact temperature being dependent upon the feed to the reactor. The reaction pressure is generally in the order of from about 1 to about 50 atmospheres.

The feed to the chlorinated hydrocarbon production reactor may be either a hydrocarbon or partially chlorinated hydrocarbon, and as representative examples of such feeds, there may be mentioned: aromatic hydrocarbons, such as benzene; aliphatic hydrocarbons, (saturated and/or olefinically unsaturated), preferably a $C_1$ to $C_4$ hydrocarbon; or a partially chlorinated derivative of such aromatic and aliphatic hydrocarbons. The most preferred feeds are ethane, ethylene, methane and partially chlorinated $C_1$ to $C_2$ hydrocarbons.

The present invention is particularly applicable to a chlorinated hydrocarbon production system directed to the production of chlorinated methanes from methane or to the production of chlorinated $C_2$ hydrocarbons from ethane and/or ethylene.

The present invention will be further described with respect to an embodiment thereof illustrated in the accompanying drawing wherein:

The drawing is a simplified schematic diagram of a lift gas system employed in a molten salt chlorinated hydrocarbon production system.

Referring now to the drawing, there is shown an oxidation reactor, generally indicated as 10; a chlorinated hydrocarbon production reactor, generally indicated as 11 and a lift gas separation vessel, generally indicated as 12. The vessel 12 is divided by a dividing wall 15 into a first molten salt lift gas separator 13 and a second molten salt-lift gas separator 14. In this manner, molten salt introduced into separator 13 is maintained separate from the molten salt introduced into separator 14.

The bottom of the oxidation reactor 10 is connected with the lift gas separator 12 through piping, generally indicated as 16, and including a lift gas pipe 17 for introducing molten salt into the molten salt separator 14 of vessel 12. The lift gas pipe 17 includes an inlet pipe 18 for introducing a lift gas pipe therein.

Similarly, the bottom of the chlorinated hydrocarbon production reactor 11 is connected to the vessel 12 through suitable piping, generally indicated as 21, which includes a lift gas pipe 22 for introducing molten salt into the separator 13. The lift gas pipe includes a lift gas inlet 23 for introducing lift gas into the lift gas pipe 22.

Suitable piping, generally designated as 25, connects the separator 14 of vessel 12 with the upper portion of the chlorinated hydrocarbon production reactor 11, whereby molten salt can be withdrawn from separator 14 and introduced into the upper portion of the chlorinated hydrocarbon production reactor 11.

Similarly, suitable piping, generally designated as 26, connects the separator 13 of vessel 12 with the upper portion of the oxidation reactor 10 whereby molten salt withdrawn from the separator 13 can be introduced into the upper portion of the oxidation reactor 10.

The system is further provided with a melt storage tank 31, which is connected to the bottom of the lift gas pipe 22 through suitable piping, designated as 32, and to the bottom of the lift gas pipe 17, through suitable piping, designated as 33. The melt storage tank 31 is pressurized, during operation of the system, by a suitable gas, such as nitrogen, introduced through line 45 and which can be withdrawn through line 46. The pressure maintained in tank 31 is generally in the order of from about 2 to about 55 atm.

The flow rate of the molten salt in the lift pipes 17 and 22 is determined, in part, by the pressure in tank 31, with the flow rate being increased in response to increased pressures in tank 31. As a result, a control of the pressure in tank 31 is a convenient manner of controlling salt flow rates in lift pipes 17 and 22.

It has also been found that under normal operating conditions, as a result of the use of a pressurized tank 31, there is little flow of molten salt into and out of the melt storage tank 31. As a result, there is little mixing of the salt contents of the respective lift gas circuits. Upon shutting down of the operation, the pressure is released from tank 31, and the salt in the system flows into melt storage tank 31. Thus, a single melt storage tank permits control of flow rates, without mixing of molten salt in the separate circuits, and also provides the surge capacity and storage capacity for the system.

The chlorinated hydrocarbon production reactor 11 is provided with a suitable inlet pipe, designated as 35 for introducing feed material and an outlet pipe 36 for withdrawing a chlorinated hydrocarbon containing effluent.

The oxidation reactor 10 is provided with an inlet 41 for introducing an oxygen containing gas, and an outlet pipe 43 for withdrawing unused gases.

The lift gas separator 12 is also provided with an outlet pipe 44 for withdrawing separated lift gas.

In operation, a molten salt mixture, containing a multivalent metal chloride in its higher and lower valence state, and a melting point depressant, such as a mixture of cuprous chloride, cupric chloride and potassium chloride is countercurrently contacted in oxidation reactor 10 with an oxygen containing gas introduced through line 41. An oxidized molten salt mixture, containing cuprous chloride, cupric chloride, copper oxychloride and the melting point depressant, is withdrawn from the lower portion of reactor 10 through the piping 16. The withdrawn molten salt is lifted into the separator 14 by a suitable lift gas, such as a nitrogen containing gas, introduced into the lift pipe 17 through line 18. In the separator 14, the molten salt is separated from the lift gas, with the molten salt flowing through piping 25, into the upper portion of the chlorinated hydrocarbon production reactor 11. In reactor 11, the molten salt is countercurrently contacted with the chlorinated hydrocarbon production feed, introduced through line 35. The chlorinated hydrocarbon production feed introduced through line 35 generally includes a hydrocarbon, such as methane, chlorine and/or hydrogen chloride, and recycle components.

Molten salts is withdrawn from the lower portion of the reactor 11 through piping 21 and introduced into the separator 13 of the vessel 12 by lift gas introduced through line 23 into the gas lift pipe 22. Molten salt flows from separator 13 through piping 26 into the upper portion of the oxidation reactor 10.

The lift gas separated from the molten salt introduced into separators 13 and 14 of vessel 12 is withdrawn from the vessel 12 through piping 44.

Under normal operation, there is little flow into and out of the melt storage tank 31, and as a result, there is little mixing between the oxidized salt from the oxidation reactor 10 and the molten salt from the chlorinated hydrocarbon production reactor 11 in the melt storage tank 31.

As should be apparent, the hereinabove described embodiment can be modified within the spirit and scope of the present invention. Thus, for example, the oxidation reactor 10 and/or the chlorinated hydrocarbon production reactor 11 may be provided with inlets and outlets for introducing and withdrawing various components other than as particularly described. Thus, for example, as known in the art, the oxidation reactor 10 may also be provided with an effluent obtained from the combustion of chlorinated hydrocarbon by-products in order to recover the chlorine values therefrom by generating higher valent metal chloride.

Similarly, two separate molten salt separation vessels could be employed, instead of a single vessel having two separate compartments.

As a result, the scope of the present invention is not limited to the hereinabove described particular embodiment.

The present invention is particularly advantageous in that the use of a single pressurized melt storage tank permits control of salt flow rates, while maintaining storage and surge capacity, at reduced capital costs.

Numerous modifications and variations of the present invention are possible in light of the above teachings, and therefore, within the scope of the appended claims, the invention may be practiced otherwise than as particularly described.

What is claimed is:

1. An apparatus for producing chlorinated hydrocarbons by the use of molten salts, comprising:
   an oxidation reactor including an inlet and outlet for oxidizing molten salts;
   a chlorinated hydrocarbon production reactor including an inlet and outlet for producing chlorinated hydrocarbons;
   a first lift gas separating means;
   a first lift gas pipe connecting the lower portion of the oxidation reactor with the first lift gas separating means, said first lift gas pipe including means for introducing a lift gas therein for passing molten salt from the oxidation reactor to the first lift gas separating means;
   a second lift gas separating means;
   a second lift gas pipe connecting the lower portion of the chlorinated hydrocarbon production reactor with the second lift gas separating means, said second lift gas pipe including means for introducing a lift gas therein for passing molten salt from the chlorinated hydrocarbon reactor to the second lift gas separating means;
   first pipe means connecting the first lift gas separating means with an upper portion of the chlorinated hydrocarbon production reactor for passing molten salt from the first lift gas separating means into the chlorinated hydrocarbon production reactor;
   a second pipe means for connecting the second lift gas separating means with an upper portion of the oxidation reactor for passing molten salt from the second lift gas separating means into the oxidation reactor; and
   a pressurized melt storage tank, including a third pipe means connecting the pressurized melt storage tank with the bottom of the first lift gas pipe, a fourth pipe means connecting the pressurized melt storage tank with the bottom of the second lift gas pipe, and means for introducing and withdrawing a gas under pressure to control the pressure in the melt storage tank and thereby control the flow rates of the molten salt, and normally prevent flow of molten salt between the melt storage tank and the first and second lift gas pipes.

2. The apparatus of claim 1 wherein the first and second lift gas separating means are in a single vessel.

* * * * *